US010858329B2

(12) United States Patent
Sookraj

(10) Patent No.: US 10,858,329 B2
(45) Date of Patent: Dec. 8, 2020

(54) CATALYST RECYCLE METHODS

(71) Applicant: Novomer, Inc., Waltham, MA (US)

(72) Inventor: Sadesh H. Sookraj, Cambridge, MA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 15/308,989

(22) PCT Filed: Apr. 29, 2015

(86) PCT No.: PCT/US2015/028123
§ 371 (c)(1),
(2) Date: Nov. 4, 2016

(87) PCT Pub. No.: WO2015/171372
PCT Pub. Date: Nov. 12, 2015

(65) Prior Publication Data
US 2017/0096407 A1    Apr. 6, 2017

Related U.S. Application Data

(60) Provisional application No. 61/988,495, filed on May 5, 2014.

(51) Int. Cl.
*B01J 31/20* (2006.01)
*C07D 305/12* (2006.01)
*C07D 307/60* (2006.01)
*B01J 31/22* (2006.01)
*B01J 31/40* (2006.01)
*B01J 38/74* (2006.01)

(52) U.S. Cl.
CPC ............ *C07D 305/12* (2013.01); *B01J 31/20* (2013.01); *B01J 31/2217* (2013.01); *B01J 31/403* (2013.01); *B01J 38/74* (2013.01); *C07D 307/60* (2013.01); *Y02P 20/584* (2015.11)

(58) Field of Classification Search
CPC ....................................................... B01J 31/20
See application file for complete search history.

(56) References Cited

U.S. PATENT DOCUMENTS

| | | |
|---|---|---|
| 2,245,404 A | 6/1941 | Kise et al. |
| 2,302,321 A | 11/1942 | Hopff et al. |
| 2,469,704 A | 5/1949 | Stone |
| 2,526,554 A | 10/1950 | Gresham et al. |
| 3,002,017 A | 9/1961 | Wearsch et al. |
| 3,326,938 A | 6/1967 | Lyle |
| 3,751,435 A | 8/1973 | Van Der Ven et al. |
| 3,800,006 A | 3/1974 | Katayama et al. |
| 4,026,967 A | 5/1977 | Flexman, Jr. et al. |
| 4,081,253 A | 3/1978 | Marion |
| 4,590,293 A | 5/1986 | Pascoe |
| 4,873,378 A | 10/1989 | Murphy et al. |
| 5,096,470 A | 3/1992 | Krishnamurthy |
| 5,198,578 A | 3/1993 | Etzkorn et al. |
| 5,310,948 A | 5/1994 | Drent et al. |
| 5,359,081 A | 10/1994 | Drent et al. |
| 5,731,252 A | 3/1998 | Warner et al. |
| 6,147,126 A | 11/2000 | DeGeorge et al. |
| 6,392,078 B1 | 5/2002 | Ryu et al. |
| 6,492,535 B1 | 12/2002 | Castiglioni et al. |
| 6,573,340 B1 | 6/2003 | Khemani et al. |
| 6,773,578 B1 | 8/2004 | O'Rear et al. |
| 6,852,865 B2 | 2/2005 | Coates et al. |
| 6,916,951 B2 | 7/2005 | Tustin et al. |
| 7,420,064 B2 | 9/2008 | Luinstra et al. |
| 8,445,703 B2 * | 5/2013 | Allen .................. C07D 305/12 549/328 |
| 8,796,475 B2 * | 8/2014 | Allen .................. C07D 305/12 549/328 |
| 9,096,510 B2 | 8/2015 | Porcelli et al. |
| 9,156,803 B2 | 10/2015 | Allen et al. |
| 9,206,144 B2 * | 12/2015 | Allen .................. C07D 305/12 |
| 9,327,280 B2 | 5/2016 | Lee et al. |
| 9,403,788 B2 | 8/2016 | Lee et al. |
| 9,493,391 B2 | 11/2016 | Allen et al. |
| 9,914,689 B2 | 3/2018 | Porcelli et al. |
| 10,099,988 B2 | 10/2018 | Farmer et al. |

(Continued)

FOREIGN PATENT DOCUMENTS

CN     103822811 A    5/2014
EP     0352850 A1    1/1990

(Continued)

OTHER PUBLICATIONS

Church et al., "Carbonylation of Heterocycles by Homogeneous Catalysts", Chemical Communication, 2007, pp. 657-674.
International Preliminary Report on Patentability received for PCT Patent Application No. PCT/US2015/028123, dated Nov. 17, 2016, 6 pages.
International Search Report and Written Opinion received for PCT Patent Application No. PCT/US2015/028123, dated Jul. 23, 2015, 7 pages.
Wilen et al., "Strategies in Optical Resolutions", Tetrahedron Report No. 38, vol. 33, 1977, pp. 2725-2736.
Extended European Search Report received for European Patent Application No. 15789639.0, dated Nov. 7, 2017, 6 pages.
Ganji et al., "In Situ Generation of the Coates Catalyst: A Practical and Versatile Catalytic System for the Carbonylation of Meso-Epoxides", Organic Letters, vol. 13, No. 12, 2011, pp. 3142-3145.

(Continued)

*Primary Examiner* — John S Kenyon
(74) *Attorney, Agent, or Firm* — Young Basile Hanlon & MacFarlane, P.C.

(57) ABSTRACT

The present invention provides novel solutions to the problem of recycling carbonylation catalysts in epoxide carbonylation processes. The inventive methods are characterized in that the catalyst is recovered in a form other than as active catalyst. In some embodiments, catalyst components are removed selectively from the carbonylation product stream in two or more processing steps. One or more of these separated catalyst components are then utilized to regenerate active catalyst which is utilized during another time interval to feed a continuous carbonylation reactor.

19 Claims, No Drawings

(56) References Cited

U.S. PATENT DOCUMENTS

| | | |
|---|---|---|
| 10,099,989 B2 | 10/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2003/0098274 A1 | 5/2003 | Lee et al. |
| 2003/0162961 A1 | 8/2003 | Coates et al. |
| 2004/0102532 A1 | 5/2004 | Landis et al. |
| 2005/0014977 A1 | 1/2005 | Drent et al. |
| 2005/0196343 A1 | 9/2005 | Reddy et al. |
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2007/0155984 A1 | 7/2007 | Sielcken et al. |
| 2007/0161806 A1 | 7/2007 | Preishuber-Pflugl et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0299032 A1 | 12/2009 | Allen |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0354881 A1 | 12/2018 | Farmer et al. |
| 2018/0354882 A1 | 12/2018 | Sookraj |
| 2019/0030520 A1 | 1/2019 | Lee |
| 2019/0106532 A1 | 4/2019 | Sookraj |

FOREIGN PATENT DOCUMENTS

| | | | |
|---|---|---|---|
| EP | 0441447 A1 | 8/1991 | |
| EP | 2325214 A1 | 5/2011 | |
| GB | 762138 A | 11/1956 | |
| JP | 57-14596 A | 1/1982 | |
| WO | 2002/09781 A2 | 2/2002 | |
| WO | 2006/087556 A1 | 8/2006 | |
| WO | 2010/118128 A1 | 10/2010 | |
| WO | WO-2010118128 A1 * | 10/2010 | ........... C07D 305/12 |
| WO | 2010/137974 A1 | 12/2010 | |
| WO | 2011/123558 A1 | 10/2011 | |
| WO | 2011/163309 A2 | 12/2011 | |
| WO | 2012/030619 A1 | 3/2012 | |
| WO | 2012/158573 A1 | 11/2012 | |
| WO | 2013/063191 A1 | 5/2013 | |
| WO | 2013/067460 A1 | 5/2013 | |
| WO | 2013/068846 A1 | 5/2013 | |
| WO | WO-2013063191 A1 * | 5/2013 | |
| WO | 2013/122905 A1 | 8/2013 | |
| WO | 2013/126375 A1 | 8/2013 | |
| WO | 2013/180659 A1 | 12/2013 | |
| WO | 2013/185009 A1 | 12/2013 | |
| WO | 2014/004858 A1 | 1/2014 | |
| WO | 2014/008232 A2 | 1/2014 | |
| WO | 2015/085295 A2 | 6/2015 | |
| WO | 2015/110321 A1 | 7/2015 | |
| WO | 2015/138975 A1 | 9/2015 | |
| WO | 2015/171372 A1 | 11/2015 | |
| WO | 2015/184289 A1 | 12/2015 | |
| WO | 2016/015019 A1 | 1/2016 | |
| WO | 2016/130947 A1 | 8/2016 | |
| WO | 2016/130977 A1 | 8/2016 | |
| WO | 2016/130988 A1 | 8/2016 | |
| WO | 2016/130993 A1 | 8/2016 | |
| WO | 2016/130998 A1 | 8/2016 | |
| WO | 2016/131001 A1 | 8/2016 | |
| WO | 2016/131003 A1 | 8/2016 | |
| WO | 2016/131004 A1 | 8/2016 | |
| WO | WO-2016130998 A1 * | 8/2016 | ............. C07C 67/37 |
| WO | 2017/023777 A1 | 2/2017 | |
| WO | 2017/023820 A1 | 2/2017 | |
| WO | 2017/165344 A1 | 9/2017 | |
| WO | 2017/165345 A1 | 9/2017 | |
| WO | 2018/085251 A1 | 5/2018 | |
| WO | 2018/085254 A1 | 5/2018 | |
| WO | 2018/136638 A1 | 7/2018 | |
| WO | 2018/170006 A1 | 9/2018 | |
| WO | 2019/051184 A1 | 3/2019 | |

OTHER PUBLICATIONS

Ganji et al., "In Situ Generation of the Coatescatalyst: a Practical and Versatile Catalytic System for the Carbonylation of Meso-Epoxides", ChemInform Abstract, vol. 42, No. 39, 2011, 1 page.

Getzler et al., "Synthesis of β-Lactones: A Highly Active and Selective Catalyst for Epoxide Carbonylation", Journal of the American Chemical Society. vol. 124, No. 7, 2002, pp. 1174-1175.

International Search Report and Written Opinion received for PCT Patent Application No. PCT/US2016/017875, dated May 6, 2016, 16 pages.

International Search Report and Written Opinion received for PCT Patent Application No. PCT/US2016/017844, dated May 6, 2016, 10 pages.

International Search Report and Written Opinion received for PCT Patent Application No. PCT/US13/25683, dated Apr. 23, 2013, 8 pages.

International Search Report and Written Opinion received for PCT Patent Application No. PCT/US17/23302, dated Jun. 5, 2017, 9 pages.

International Search Report and Written Opinion received for PCT Patent Application No. PCT/US17/23303, dated Jun. 7, 2017, 18 pages.

International Search Report and Written Opinion received for PCT Patent Application No. PCT/US2010/030230, dated Jun. 10, 2010, 17 pages.

(56) References Cited

OTHER PUBLICATIONS

International Search Report and Written Opinion received for PCT Patent Application No. PCT/US11/49125, dated Jan. 11, 2012, 10 pages.
International Search Report and Written Opinion received for PCT Patent Application No. PCT/US2012/037675, dated Aug. 9, 2012, 12 pages.
International Search Report and Written Opinion received for PCT Patent Application No. PCT/US2012/061791, dated Feb. 8, 2013, 10 pages.
International Search Report and Written Opinion received for PCT Patent Application No. PCT/US2013/026810, dated Apr. 30, 2013, 8 pages.
International Search Report and Written Opinion received for PCT Patent Application No. PCT/US2013/048238, dated Dec. 3, 2013, 8 pages.
International Search Report and Written Opinion received for PCT Patent Application No. PCT/US2013/049026, dated Dec. 17, 2013, 9 pages.
International Search Report and Written Opinion received for PCT Patent Application No. PCT/US2014/069066, dated Mar. 16, 2015, 10 pages.
International Search Report and Written Opinion received for PCT Patent Application No. PCT/US2015/020562, dated Jun. 18, 2015, 9 pages.
International Search Report and Written Opinion received for PCT Patent Application No. PCT/US2015/042124, dated Dec. 15, 2015, 14 pages.
International Search Report and Written Opinion received for PCT Patent Application No. PCT/US2016/017797, dated May 5, 2016, 9 pages.
International Search Report and Written Opinion received for PCT Patent Application No. PCT/US2016/017861, dated Apr. 29, 2016, 25 pages.
International Search Report and Written Opinion received for PCT Patent Application No. PCT/US2016/017868, dated May 2, 2016, 9 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/017881, dated May 2, 2016, 8 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2017/059243, dated Feb. 1, 2018, 10 pages.
International Search Report and Written Opinion received for PCT Patent Application No. PCT/US2015/033232, dated Aug. 19, 2015, 8 pages.
Rowley et al., "Catalytic Double Carbonylation of Epoxides to Succinic Anhydrides: Catalyst Discovery, Reaction Scope, and Mechanism", Journal of the American Chemical Society, vol. 129, No. 16, 2007, pp. 4948-4960.
Slowik et al., "Catalytic Conversion of Waste Carbon Monoxide to Valuable Chemicals & Materials", Clean Technology, 2010, pp. 283-286.
Stanghellini et al., "Redox Reactions of Metal Carbonyls. I. Kinetics and Mechanism of Disproportionation of $Co_2(Co)_8$ with Piperidine", Inorganica Chimica Acta, vol. 22, 1977, pp. 19-22.
Trimm, D. L., "Minimisation of Carbon Monoxide in a Hydrogen Stream for Fuel Cell Application", Applied Catalysis A: General, vol. 296, 2005, 11 pages.
"Understanding Biobased Carbon Content", Society of the Plastics Industry Bioplastics Council, Feb. 2012, pp. 1-12.

\* cited by examiner

CATALYST RECYCLE METHODS

CROSS-REFERENCE TO RELATED APPLICATIONS

This application is a U.S. National Phase patent application of PCT/US2015/028123, filed Apr. 29, 2015, which claims the benefit of U.S. Provisional Patent Application Ser. No. 61/988,495, filed May 5, 2014, the disclosures of which are hereby incorporated herein by reference in their entirety.

BACKGROUND OF THE INVENTION

The production of three- and four-carbon commodity chemicals such as acrylic acid (AA), butane diol (BDO), and tetrahydrofuran (THF) from low priced two-carbon feedstocks is of increasing interest. The appeal of the approach stems from the ability to substitute low cost ethane-derived feedstocks for the propylene and butane currently used in production of C3s and C4s respectively. The discovery and exploitation of huge shale gas reserves rich in ethane has made this approach even more compelling since ethane prices are falling while propylene prices have tended to increase along with petroleum.

One particularly promising process in this vein relies on the carbonylation of ethylene oxide to produce AA (via propiolactone or polypropiolactone) or BDO and THF via succinic anhydride. A number of catalysts have been investigated for this process, the most active of which are the carbonylation catalysts developed by Geoff Coates and coworkers at Cornell University. The Coates catalysts are homogenous catalysts combining a cationic Lewis acid and an anionic metal carbonyl. These catalysts demonstrate high product selectivity and relatively high rates as compared to prior catalysts such as those based on cobalt carbonyls in combination with pyridine derivatives or neutral Lewis acids such as $BF_3$.

Nevertheless, a major challenge in commercializing ethylene oxide carbonylation is the development of a viable continuous production process. To be economical, the carbonylation catalyst must be capable of turning over tens or hundreds of thousands of equivalents of epoxide. To achieve such turnover numbers it is probable that an efficient catalyst recycle loop will be required. Several such processes have been described including: removal of carbonylation product by distillation from a solution of catalyst in a high boiling solvent as described in WO 2010/118128; selective retention of catalyst in the reactor by nanofiltration WO 2014/008232; separation of product from a catalyst solution by crystallization WO 2012/030619, and WO 2013/122905; and immobilization of the catalyst on a solid support, WO/2013063191.

A key challenge is the tendency for the carbonylation catalyst to decompose in a CO-depleted atmosphere, and/or the propensity of the metal carbonyl portion of the catalyst to become disassociated from other catalyst components such as a Lewis acid or heterocycle. The present invention provides solutions to this and other related problems.

SUMMARY OF THE INVENTION

In a first aspect, the present invention provides novel solutions to the problem of recycling carbonylation catalysts in epoxide carbonylation processes. In the broadest sense, the inventive methods are differentiated from prior art attempts to solve this problem by the fact that the inventive catalyst recycle regime does not occur in real-time. Whereas previous attempts to recycle the catalysts from epoxide carbonylation processes have featured catalyst recycle loops where the catalyst is retrieved from the reaction product stream in a catalytically active form which is continuously fed back to the carbonylation reactor, the present methods are differentiated by the fact that the catalyst (or indeed inactive catalyst products or components) are separated and accumulated over some interval of time and then utilized in the carbonylation process at a later time. The intervals of time over which the catalyst is accumulated typically range from hours to days and are longer than the typical loop transport or processing times in existing processes which are normally on the order of minutes.

In certain embodiments, the inventive methods are characterized in that the catalyst is recovered in a form other than as active catalyst. In some embodiments, catalyst components are removed selectively from the carbonylation product stream in two or more processing steps. One or more of these separated catalyst components are then utilized to regenerate active catalyst which is utilized during another time interval to feed a continuous carbonylation reactor. For example, in certain embodiments a method such as ion exchange is used to selectively remove an ionic component of a carbonylation catalyst (for example the cationic Lewis acid) to the exclusion of other catalyst components (for example an anionic metal carbonyl) which can be separated in a later step and accumulated separately to be re-used or disposed of.

One advantage of the present methods is elimination of costly equipment and processes necessary to recover the active catalysts which are typically oxygen sensitive, thermally unstable, unstable in the atmospheres lacking carbon monoxide, and in some cases reactive toward the carbonylation products at elevated temperatures. By removing the requirement that the catalyst be recovered in active form, the present invention provides substantial advantages in terms of the complexity and cost of the catalyst recovery steps.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the abovementioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "glycidyl", as used herein, refers to an oxirane substituted with a hydroxyl methyl group or a derivative thereof. The term glycidyl as used herein is meant to include moieties having additional substitution on one or more of the carbon atoms of the oxirane ring or on the methylene group of the hydroxymethyl moiety, examples of such substitution may include, but are not limited to: alkyl groups, halogen atoms, aryl groups etc. The terms glycidyl ester, glycidyl acrylate, glydidyl ether etc. denote substitution at the oxygen atom of the above-mentioned hydroxymethyl group, i.e. that oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, spiro[4.5]decane, The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl mono or polycyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-4}C(O)N(R^\circ)_2$; —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —C(O)$SR^\bullet$, —$(C_{1-4}$ straight or branched alkylene)C(O)$OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =NNHC(O)$R^*$, =NNHC(O)$OR^*$, =$NNHS(O)_2R^*$, =$NR^*$, =$NOR^*$, —O(C($R^*_2$))$_{2-3}$O—, or —S(C($R^*_2$))$_{2-3}$S—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(C$R^*_2$)$_{2-3}$O—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ include halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —$R^\dagger$, —$NR^\dagger_2$, —C(O)$R^\dagger$, —C(O)$OR^\dagger$, —C(O)C(O)$R^\dagger$, —C(O)$CH_2C(O)R^\dagger$, —$S(O)_2R^\dagger$, —$S(O)_2NR^\dagger_2$, —C(S)$NR^\dagger_2$, —C(NH)$NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

"Tetradentate" refers to ligands having four sites capable of coordinating to a single metal center.

As used herein, the term "about" preceding one or more numerical values means the numerical value ±5%.

DETAILED DESCRIPTION OF THE INVENTION

Methods of the Invention

In a first aspect, the present invention provides methods for the continuous reaction of an epoxide and carbon monoxide. The methods utilize a carbonylation reactor in which the epoxide and carbon monoxide are contacted in the presence of a carbonylation catalyst to produce a reaction product stream. Typically, the reactor is fed with at least three input streams: an epoxide feedstream, a carbon monoxide feed, and a catalyst feedstream (though in certain embodiments additional feeds may be present, or two or more streams may be combined to lessen the total number of separate feed streams). The reaction product stream exits the reactor and contains epoxide carbonylation products, the catalyst, and optionally unreacted feedstock, solvent, reaction byproducts and the like. In certain embodiments, the epoxide carbonylation product comprises a beta lactone, a succinic anhydride, or a polyester. In certain embodiments, the epoxide carbonylation product is not a 3-hydroxy propionic acid or a 3-hydroxy propionaldehyde.

In certain embodiments, methods of the present invention include the steps of:
  a) feeding a continuous carbonylation reactor during a first interval of time with a catalyst feed stream comprising a carbonylation catalyst, an epoxide feedstream comprising an epoxide, and carbon monoxide such that within the reactor the epoxide and carbon monoxide react under the influence of the carbonylation catalyst to form a carbonylation reaction product selected from the group consisting of: a beta lactone, a succinic anhydride, or a polyhydroxypropionate, such that a reaction product stream comprising the epoxide carbonylation product and the carbonylation catalyst, continuously exits the reactor,
  b) treating the reaction product stream to separate at least a portion of the carbonylation catalyst,
  c) accumulating carbonylation catalyst collected in step (b) throughout the first interval of time to obtain a spent carbonylation catalyst batch,
  d) feeding a continuous carbonylation reactor during a second interval of time with a catalyst feed stream wherein at least a portion of the catalyst in the catalyst feed stream comprises (or is derived at least in part from) the spent carbonylation catalyst batch accumulated in step (c).

In certain embodiments, the step of treating the reaction product stream to separate a portion of the carbonylation catalyst entails using a separation mode selected from the group consisting of: precipitation, adsorption, ion exchange, extraction, and any combination of two or more of these.

In certain embodiments, the step of treating the reaction product stream to separate a portion of the carbonylation catalyst entails precipitating the catalyst. Precipitation of the catalyst can be accomplished by any known means. Suitable means of precipitating the catalyst will be apparent to the skilled chemist and may include, but are not limited to: adding a solvent to the reaction product stream in which the catalyst (or a component thereof) is poorly soluble, cooling the reaction product stream, adding a material that interacts with the catalyst (or a component thereof) to form an insoluble adduct, removing solvent, excess feedstock, or carbon monoxide from the reaction product stream, and combinations of any two or more of these.

In certain embodiments where the step of treating the reaction product stream to separate a portion of the carbonylation catalyst entails precipitation, the precipitation step comprises adding a solvent in which the catalyst (or a component of the catalyst) is poorly soluble. In certain embodiments, a non-polar solvent such as an aliphatic hydrocarbon, an aromatic hydrocarbon, or condensed phase $CO_2$ is added to precipitate the catalyst. In certain embodiments, a solvent selected from butane, pentane, hexane, heptane, octane, cyclopentane, cyclohexane, decalin, higher alkanes, and mixtures of two or more alkanes is added to the reaction product stream to precipitate the catalyst or a catalyst component. In certain embodiments, a solvent selected from benzene, toluene, xylene, mesitylene, chlorobenzene, or other substituted benzene compounds is added to the reaction product stream to precipitate the catalyst or a catalyst component. In certain embodiments, supercritical $CO_2$ is added to the reaction product stream to precipitate the catalyst or a catalyst component. In certain embodiments where the carbonylation catalyst comprises the combination of a Lewis acidic metal complex and a metal carbonyl compound and a non-polar solvent is added to the reaction product stream, this causes precipitation of the Lewis acidic metal complex but leaves at least a portion of the metal carbonyl component of the catalyst behind in the reaction product stream.

In embodiments where the catalyst is precipitated, the step of separating the carbonylation catalyst typically includes further steps to remove the precipitate from the product stream, such isolation steps are well known in the art and can include, but are not limited to filtration, sedimentation, centrifugation, coagulation, and combinations of two or more of these.

Therefore, in certain embodiments, the present invention encompasses methods having the steps of:
  a) feeding a continuous carbonylation reactor during a first interval of time with a catalyst feed stream comprising a carbonylation catalyst, an epoxide feed stream comprising an epoxide, and carbon monoxide such that within the reactor, the epoxide and carbon monoxide react under the influence of the carbonylation catalyst to form a carbonylation reaction product selected from the group consisting of: a beta lactone, a succinic anhydride, and a polyhydroxypropionate, wherein a reaction product stream comprising the epoxide carbonylation product and the carbonylation catalyst exits the reactor,
  b) adding to the reaction product stream a solvent selected from the group consisting of: condensed phase $CO_2$, an alkane, an aliphatic hydrocarbon, and an aromatic hydrocarbon thereby causing at least a portion of the carbonylation catalyst to precipitate from the reaction product stream and separating the precipitated carbonylation catalyst from the reaction product stream,
c) accumulating carbonylation catalyst collected in step (b) throughout the first interval of time to obtain a spent carbonylation catalyst batch,
d) feeding a continuous carbonylation reactor during a second interval of time with a catalyst feed stream wherein at least a portion of the catalyst in the catalyst feed stream comprises (or is derived at least in part from) the spent carbonylation catalyst batch accumulated in step (c).

In certain embodiments, the step of treating the reaction product stream to separate carbonylation catalyst comprises adsorbing the catalyst or catalyst components. The step of adsorption can entail treating the reaction product stream with a solid adsorbing material. Suitable solid adsorbing materials include inorganic substances, activated carbon, polymers, resins, or any combination of two or more of these. Suitable inorganic adsorbing materials include silica gel, alumina, silicate minerals, clays, diatomaceous earth, Fuller's earth, ceramics, zirconias, molecular sieves and the like. Suitable polymers include polystyrenes, polyacrylonitrile, polyimides, polyolefins, polyesters, polyethers, polycarbonates, polyisocyanates, and the like. Such polymers optionally include additional chemical functional groups to enhance their ability to adsorb carbonylation catalysts or catalyst components. Such functional groups can include acids (i.e. sulfonic or carboxylic acids), coordinating groups (i.e. amine, thiol, phosphine, nitrile, or boron groups), bases, (for example amine groups or nitrogen heterocycles). In certain cases, the adsorbing materials whether inorganic or polymeric are acidic, basic, or have undergone chemical treatments to enhance the affinity of the catalyst.

In embodiments where catalyst is removed from the reaction product stream by adsorption, the adsorbant can be contacted with the product stream by any conventional method. This includes, but is not limited to: flowing the reaction product stream through a fixed bed of adsorbent; flowing the reaction product stream through a fluidized bed of adsorbant; flowing the reaction product stream through fabrics, meshes, or filtration plates comprising the adsorbant material; or slurrying the reaction product stream with the adsorbant material (typically followed by filtration, centrifugation, sedimentation or the like to remove the adsorbant from the product stream). In embodiments where the reaction product stream is flowed through a column of adsorbant, it may be desirable to provide a plurality of such columns in parallel with a provision to switch the flow from one column to another. Thus when one column of adsorbant becomes saturated with catalyst, it can be switched out of the flow path and the flow diverted to a fresh column—in certain embodiments, the interval of time from when a column is placed in the flow path to when it is switched out of the flow path corresponds to the "first time interval" recited in the methods described herein.

Where an adsorbant is used to remove catalyst from the reaction product stream, the inventive methods will typically include a step of desorbing the catalyst or catalyst component(s) from the adsorbant. Such desorption methods are well known in the art and will vary depending on the identity of the adsorbant and the catalyst. Desorption can include treating with a polar solvent or solute which displaces the catalyst or catalyst component, or can comprise a reactive process where the a reagent is added to the adsorbed catalyst to regenerate it or form a species which is less adhered to the adsorbing solid.

Therefore, in certain embodiments, the present invention encompasses methods having the steps of:
a) feeding the continuous carbonylation reactor during a first interval of time with a catalyst feed stream comprising a carbonylation catalyst, an epoxide feedstream comprising an epoxide, and carbon monoxide such that within the reactor, the epoxide and carbon monoxide react under the influence of the carbonylation catalyst to provide a reaction product stream exiting the reactor and comprising an epoxide carbonylation product and carbonylation catalyst,
b) contacting the reaction product stream with a solid material which adsorbs at least a portion of the carbonylation catalyst from the reaction product stream,
c) accumulating carbonylation catalyst adsorbed in step (b) throughout the first interval of time and processing it to obtain a spent carbonylation catalyst batch,
d) feeding a continuous carbonylation reactor during a second interval of time with a catalyst feed stream wherein at least a portion of the catalyst in the catalyst feed stream comprises (or is derived at least in part from) the spent carbonylation catalyst batch accumulated in step (c).

In certain embodiments, the step of treating the reaction product stream to separate carbonylation catalyst comprises ion exchange of the catalyst or catalyst components. In certain embodiments, the step of treating the reaction product stream to separate carbonylation catalyst comprises treating the reaction product stream with ion exchange materials. The ion exchange materials may be cationic, anionic, amphoteric, Lewis basic, Lewis acidic or may comprise chelating groups. In certain embodiments, the ion exchange material may be a cation exchanger. In certain embodiments, functional groups on the cation exchange materials may be selected from the group: $-SO_3\bar{o}$, $PO_3^{2-}$, $-COOH$, $-C_6H_4OH$, $-SH$, $-AsO_3\bar{o}$, $-SeO_3\bar{o}$, or combinations of two or more of these. In certain embodiments, functional groups on the cation exchange materials comprise $-SO_3.\bar{o}$ In certain embodiments, the ion exchange material may be an anion exchanger. In certain embodiments, functional groups on the anion exchange materials may be selected from the group: $-N^+(alkyl)_3$, $-N^+(CH_3)_3$, $-N^+(CH_3)_2C_2H_4OH$, $-N^+(CH_3)_2C_2H_5$, $-P^+(alkyl)_3$, $-P^+(aryl)_3$, $-P^+(C_4H_9)_3$, $-P^+(Ph)_3$, or combinations of two or more of these. In certain embodiments, functional groups on the anion exchange materials comprise $-N^+(alkyl)_3$. In certain embodiments, functional groups on the anion exchange materials comprise $-P^+(alkyl)_3$. In certain embodiments, functional groups on the anion exchange materials comprise $-P^+(aryl)_3$.

In certain embodiments where the step of treating the reaction product stream to separate carbonylation catalyst comprises ion exchange, the process entails both anion exchange and cation exchange. In certain embodiments, where the carbonylation catalyst comprises the combination of a cationic Lewis acid and an anionic metal carbonyl, each is removed separately and the method comprises treating the reaction product stream with a cation exchange material to remove the Lewis acid and an anion exchange material to remove the metal carbonyl. In certain embodiments the anion and cation exchange are performed concomitantly. In certain embodiments, the anion and cation exchange are performed sequentially. In certain embodiments, the anion exchange is performed first followed by cation exchange. In certain embodiments, the cation exchange is performed first followed by anion exchange.

In certain embodiments, an ion exchange material used in the separation step comprises an organic ion exchange resin. Organic ion exchange resins generally possess a three dimensional structure, a matrix. Functional groups maybe attached to the structure, or directly incorporated in the polymeric chains. The matrix may be constructed from linear polymeric chains cross-linked with each other by relatively short links. By way of example, in various aspects, the present disclosure includes the use of ion exchange materials comprised of sulphonated polystyrene cross-linked with divinylbenzene:

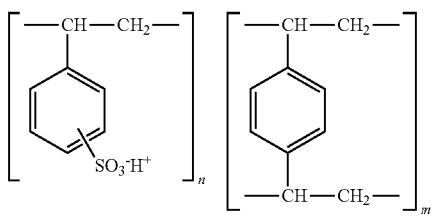

In various aspects, ion exchange materials may take the form of gels, or gel resins, distributed across a bead, or other support substrate. In various aspects, ion exchange materials may take the form of macroporous resins which have a heterogeneous structure consisting of two phases, a gel region comprised of polymers and macroscopic permanent pores. In various embodiments of the present disclosure, the ion exchange materials comprise macroreticular resins which are additionally macroporous resins in which the gel regions consist of a plurality bead micro-grains. Ion exchange materials may comprise a wide variety of morphologies and forms, including variations in porosity and other surface properties. In various aspects, materials can be formed into, but not limited to beads, pellets, spheres, spheroids, rings, hollow cylinders, blocks, fibers, meshes, membranes, textiles. In various aspects, the bead size may be widely distributed, or may be very narrow, so-called mono-disperse resins.

In embodiments where catalyst is removed from the reaction product stream by ion exchange, the ion exchange material can be contacted with the product stream by any conventional method. This includes, but is not limited to: flowing the reaction product stream through a fixed bed of a solid ion exchange material (i.e. in the form of beads, granules or other particles); flowing the reaction product stream through a fluidized bed of adsorbant, flowing the reaction product stream through fabrics, meshes, or filtration plates comprising the ion exchange material, or slurrying the reaction product stream with the ion exchange material (typically followed by filtration, centrifugation, sedimentation or the like to remove the ion exchange material from the product stream). In embodiments where the reaction product stream is flowed through a packed column of ion exchange material, it may be desirable to provide a plurality of such columns in parallel with a provision to switch the flow from one to another periodically. Thus when one column of ion exchange material becomes saturated with catalyst, it can be switched out of the flow path and the flow diverted to a fresh column—in certain embodiments, the interval of time from when a column is placed in the flow path to when it is switched out of the flow path corresponds to the "first time interval" recited in the methods described herein.

Where an ion exchange material is used to remove catalyst from the reaction product stream, the inventive methods will typically include a subsequent step of removing the catalyst or catalyst component(s) from the ion exchange material. Such removal methods are well known in the art and typically involve contacting the ion exchange resin with a strong solution of a salt, the anion or cation of which will displace the catalyst component from the ion exchange material. The specifics of this removal step will obviously vary depending on the identity of the adsorbant and the catalyst, but suitable methods are widely known to those skilled in the art.

Therefore, in certain embodiments, the present invention encompasses methods having the steps of:
  a) feeding the continuous carbonylation reactor during a first interval of time with a catalyst feed stream comprising a carbonylation catalyst, an epoxide feedstream comprising an epoxide, and carbon monoxide such that within the reactor, the epoxide and carbon monoxide react under the influence of the carbonylation catalyst to provide a reaction product stream exiting the reactor and comprising an epoxide carbonylation product and carbonylation catalyst,
  b) contacting the reaction product stream with a first ion exchange material which captures at least one component of the carbonylation catalyst from the reaction product stream,
  c) accumulating carbonylation catalyst in step (b) throughout the first interval of time and processing the ion exchange material(s) to obtain a spent carbonylation catalyst batch, and
  d) feeding a continuous carbonylation reactor during a second interval of time with a catalyst feed stream wherein at least a portion of the catalyst in the catalyst feed stream comprises (or is derived at least in part from) the spent carbonylation catalyst batch accumulated in step (c).

In certain embodiments, step (b) of the method includes the further step of treating the reaction product stream with a second ion exchange resin to remove one or more additional components of the carbonylation catalyst from the reaction product stream. In such embodiments, one or both of the ion exchange resins may be processed in step (c) to obtain the spent catalyst batch or batches.

Therefore, in certain embodiments, the present invention encompasses methods having the steps of:
  a) feeding the continuous carbonylation reactor during a first interval of time with a catalyst feed stream comprising a carbonylation catalyst, an epoxide feedstream comprising an epoxide, and carbon monoxide such that within the reactor, the epoxide and carbon monoxide react under the influence of the carbonylation catalyst to provide a reaction product stream exiting the reactor and comprising an epoxide carbonylation product and carbonylation catalyst,
  b) contacting the reaction product stream with a first ion exchange material which captures at least one component of the carbonylation catalyst from the reaction product stream, and then treating the reaction product stream with a second ion exchange material that removes one or more additional components from the reaction product stream, wherein if the first ion exchange material is an anion exchanger, then the second ion exchanger is a cation exchanger or vice versa,
  c) accumulating the removed carbonylation catalyst in step (b) throughout the first interval of time and processing at least one of the ion exchange materials to obtain a spent carbonylation catalyst batch, and d) feeding a continuous carbonylation reactor during a second interval of time with a catalyst feed stream wherein at least a portion of the catalyst in the catalyst feed stream comprises (or is derived at least in part from) the spent carbonylation catalyst batch accumulated in step (c).

In certain embodiments carbonylation catalyst is removed from the reaction product stream by extraction. In such embodiments, the extraction step comprises adding a solvent in which the catalyst (or a component of the catalyst) is soluble. In other embodiments, the extraction solvent is one in which the product is soluble, but which has little tendency to dissolve the carbonylation catalyst (or one or more components of the carbonylation catalyst). Preferably, in either case, the addition of the extraction solvent results in the formation of two phases.

In certain embodiments, the extraction solvent is a highly polar solvent such as water or an ionic liquid. In certain embodiments, the extraction solvent is supercritical $CO_2$. In certain embodiments, the extraction solvent is water or an aqueous solution. In certain embodiments, the extraction solvent is an ionic liquid. In certain embodiments where the solvent is an ionic liquid, the ionic liquid has a formula [$Cat^+$][$X^-$] wherein [$Cat^+$] refers to one or more organic cationic species; and [$X^-$] refers to one or more anions. In certain embodiments, [$Cat^+$] is selected from the group consisting of: ammonium, tetralkylammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium, uronium, and any combination of two or more of these. In accordance with the present invention, [$X^-$] may comprise an anion selected from halides, sulphates, sulfonates, sulfonimides, phosphates, phosphonates, carboxylates, $CN^-$, $NO_3^-$, $NO_2^-$, $BF_4^-$ and $PF_6^-$.

Therefore, in certain embodiments, the present invention encompasses methods having the steps of:
a) feeding the continuous carbonylation reactor during a first interval of time with a catalyst feed stream comprising a carbonylation catalyst, an epoxide feedstream comprising an epoxide, and carbon monoxide such that within the reactor, the epoxide and carbon monoxide react under the influence of the carbonylation catalyst to provide a reaction product stream exiting the reactor and comprising an epoxide carbonylation product and carbonylation catalyst,
b) adding to the reaction product stream an extraction solvent selected from the group consisting of: water, condensed phase $CO_2$, and an ionic liquid, thereby causing formation of two phases wherein the carbonylation catalyst (or at least one component of the carbonylation catalyst) is at least to some extent partitioned from the carbonylation reaction product across the two phases,
separating and treating a phase containing carbonylation catalyst (or a component of the carbonylation catalyst) to recover the catalyst or catalyst or catalyst component,
c) accumulating carbonylation catalyst or component collected in step (b) throughout the first time interval to obtain a spent carbonylation catalyst batch,
d) feeding a continuous carbonylation reactor during a second interval of time with a catalyst feed stream wherein at least a portion of the catalyst in the catalyst feed stream comprises (or is derived at least in part from) the spent carbonylation catalyst batch accumulated in step (c).

The Accumulating Step

As noted above, one of the features of methods of the present invention is accumulation of recovered carbonylation catalyst throughout a time interval. In the present methods, the carbonylation catalyst (or a component thereof) separated from the reaction product stream is accumulated through some interval of time. The accumulated catalyst (or component) forms a spent catalyst batch that is eventually reused (either in whole or in part) in a carbonylation process. The process for which the catalyst is re-used may or may not be the same process from which the catalyst was isolated. Likewise it may be reused for the same process but on another day or in a different reactor. This is in stark contrast to prior art methods wherein the separated catalyst is treated as a stream within the reaction process which is returned to the reactor within a relatively short period.

One potential advantage of the present methods is the removal of the constraint that the catalyst be recovered in active form. For examples, many carbonylation catalysts used in the processes described herein contain metal carbonyl species which are known to have limited stability under conditions lacking a pressurized atmosphere of CO. Therefore in certain embodiments of the present methods, the carbonlyation catalyst is recovered in a form other than as active catalyst. To complete the catalyst recycle method in such embodiments one or more additional steps to regenerate the catalyst must be performed.

In certain embodiments, where the carbonylation catalyst comprises a cationic Lewis acid in combination with an anionic metal carbonyl, the cationic Lewis acid portion of the catalyst is captured from the carbonylation stream without the associated metal carbonyl. This is feasible since the Lewis acid portion of the catalyst is typically the most expensive catalyst component. In certain embodiments, the cationic Lewis acid is accumulated in a form with a counterion other than the anionic metal carbonyl. In such embodiments, the methods may include a further step of treating the accumulated batch of cationic Lewis acid under conditions to swap a non metal carbonyl anion associated with the accumulated Lewis acid with a metal carbonyl anion.

In certain embodiments, where the carbonylation catalyst comprises a cationic Lewis acid in combination with an anionic metal carbonyl, the metal carbonyl portion of the catalyst is captured from the carbonylation stream without the associated Lewis acid. The metal carbonyl thus accumulated may be captured as an anionic metal carbonyl (for example by anion exchange) or it may be accumulated in another form such as a reduced metal species, a metal salt, a neutral metal carbonyl, a mixed metal carbonyl complex, or some other form. In such embodiments, the methods may include a further step of treating the accumulated species to regenerate a catalytically active metal carbonyl compound.

In the case where an intact metal carbonyl anion is accumulated (for example by capture on an anion exchange resin), such steps may include metathesis to free the metal carbonyl anion from the resin. This will typically entail flooding the resin with another anion (such as sodium chloride) to displace the metal carbonyl. The metal carbonyl may then be obtained as its sodium salt and utilized to produce active catalyst according to known catalyst synthesis procedures. Therefore, in certain embodiments, methods of the present invention comprise further steps of freeing accumulated metal carbonyl anion from a resin. In certain embodiments, such steps entail further steps of utilizing accumulated metal carbonyl anion to regenerate active catalyst by combining the accumulated metal carbonyl with a suitable Lewis acid.

In certain embodiments, the metal carbonyl may be accumulated in a form other than as an intact metal carbonyl anion. For example, in CO-deficient atmospheres, the metal carbonyl may lose one or more CO ligands to form multinuclear metal carbonyl species, salts, or precipitate in elemental form. In other embodiments, a strong ligand may utilized to displace one or more CO ligands and aid in capture of the metal carbonyl as a new complex. It is well known that such species can be utilized to regenerate well defined metal carbonyl compounds by treatment under CO pressure. Therefore, in certain embodiments, methods of the present invention include further steps of regenerating the catalytically active metal carbonyl species from a non-catalytically active material accumulated from the reaction product stream. In certain embodiments, such steps entail further steps of treating accumulated residue derived from a catalytically active metal carbonyl compound under conditions to regenerate a catalytically active metal carbonyl suitable for reuse. In certain embodiments, such steps include a step of treating the accumulated residue under high CO pressure. In certain embodiments, methods include the step of treating a cobalt-containing residue accumulated from the reaction product stream under conditions of high CO pressure to convert it to dicobalt octacarbonyl.

In certain embodiments where the accumulation of catalyst separated from the reaction product stream comprises steps of recovering two or more separate catalyst components in separate recovered catalyst batches, methods of the present invention comprise additional steps of recombining recovered catalyst components to produce active carbonylation catalyst. In some cases the recovered catalyst components may be combined directly while in other steps one or more of the components may require processing as described above prior to the step of combining. In certain embodiments such steps entail a metathesis to recombine a recovered cationic Lewis acid with a recovered metal carbonyl anion such as a carbonyl cobaltate.

Another feature of the accumulation step is that it occurs during a time interval during which the reactor is being fed and product is being withdrawn, meaning that none of the catalyst accumulated is recycled during the interval. The time interval required to accumulate a batch is dependent on the mode of accumulation, and the scale and economics of any processes required to transform the accumulated catalyst residue into active catalyst. Typically the time interval for accumulation of the catalyst or residue is on the order of hours to days, but may even be weeks. Therefore in certain embodiments of any of the methods described above, the first time interval is in the range from about 1 hour to about 200 hours. In certain embodiments, the first time interval is from about 2 hours to about 8 hours, from about 4 hours to about 16 hours, from about 12 hours to about 24 hours, or from about 16 hours to about 36 hours. In certain embodiments, the first time interval is from about 1 day to about 20 days, from about 1 day to about 3 days, from about 2 days to about 5 days, from about 5 days to about 10 days, or from about 10 days to about 20 days.

During this time, the carbonylation reactor is fed from a reservoir of catalyst which is depleted as the amount of accumulated catalyst (or catalyst residue) increases on the back end of the process. Additional time is then typically required to process the accumulated catalyst or catalyst residue to remanufacture active catalyst. Therefore some multiple of the first time interval will have elapsed from the first time interval when the catalyst was accumulated to the later time at which the carbonylation reactor is fed with a catalyst feed stream containing catalyst derived from the catalyst accumulated during the first time interval (i.e. step (d)). In certain embodiments the length of time between the second time interval (during with catalyst recovered in step (c) is fed to reactor as recited in step (d) of the methods above), and the first time interval (during which the catalyst was accumulated) is on the order of about 1 to about 100 times the length of the first time interval. In other words if the first time interval is 10 hours, the second time interval would occur from about 10 hours to about 2000 hours after the completion of the accumulation step. In certain embodiments, the length of time between the second time interval and the first time interval is from about 1 to about 10 times the length of the first time interval. In certain embodiments, the length of time between the second time interval and the first time interval is from about 1 to about 3 times, from about 2 to about 5 times, from about 4 to about 10 times, from about 10 to about 50 times, from about 40 to about 80 times, or from about 50 to about 100 times, the length of the first time interval. In certain embodiments, the length of time between the second time interval and the first time interval is greater than 100 times the first time interval.

Additional Processing Steps

In certain embodiments, methods encompassed by the present invention comprise additional steps to isolate the carbonylation product from the reaction product stream. These steps are generally executed after step (b) of the methods described above and typically entail further treatment of the product stream from which the catalyst or catalyst component has been substantially removed.

The precise mode of carrying out the carbonylation product isolation will obviously depend on the character of the carbonylation product. Suitable isolation methods include but are not limited to; distillation, crystallization, precipitation, evaporation, and the like. In embodiments where the carbonylation product is a liquid such as betapropiolactone or betabutyrolactone, the methods may comprise an additional step of performing distillation to separate the lactone from other components of the reaction product stream. Such other components can include solvent(s), unreacted epoxide, reaction byproducts, catalyst residues and the like. In embodiments where the solvent has a lower boiling point than the lactone, or where unreacted epoxide is present, the beta lactone may be retained as the bottoms in the distillation with the solvent and/or epoxide taken to the vapor phase. In embodiments, where the solvent has a boiling point higher than the lactone and/or where involatile catalyst residues are present, the lactone may be taken to the vapor phase. In certain embodiments the catalyst and/or unreacted epoxide are captured and fed back to the epoxide carbonylation reactor (either in real time, or via accumulation and use at a later time).

In embodiments where the carbonylation product is a solid such as succinic anhydride or polypropiolactone, the methods may comprise an additional step of performing a crystallization or precipitation to separate the carbonylation product from other components of the reaction product stream. Such other components can include solvent(s), unreacted epoxide, reaction byproducts, catalyst residues and the like. In certain embodiments, such methods include a step of lowering the temperature of the reaction product stream. In certain embodiments, such methods include removing solvent, excess epoxide and/or unreacted CO from the reaction product stream. In certain embodiments, such methods comprise adding a solvent to the reaction product stream to cause precipitation or crystallization of the carbonylation product.

In certain embodiments, the methods described above may include additional steps intermediate between the carbonylation reactions in step (a) and the catalyst separations in step (b). In certain embodiments, such steps include reduction of the CO pressure. In certain embodiments, the CO pressure is reduced to atmospheric pressure. In certain embodiments, excess CO is removed by exposure to subatmospheric pressures or by sweeping with another gas. In certain embodiments, the CO thus liberated is captured for re-use or is incinerated to provide heat. In certain embodiments, the methods comprise heating or cooling the reaction product stream between steps (a) and (b). When methods include separation of a solid carbonylation product, they will typically include additional substeps such as filtration, washing and collection of the solid product.

Epoxide Feedstock

In certain embodiments, the epoxide in the epoxide feedstream in any of the methods described above has a formula:

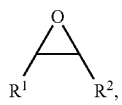

(I)

where,
R$^1$ and R$^2$ are each independently selected from the group consisting of: —H; optionally substituted C$_{1-6}$ aliphatic; optionally substituted phenyl; optionally substituted C$_{1-6}$ heteroaliphatic; optionally substituted 3- to 6-membered carbocycle; and optionally substituted 3- to 6-membered heterocycle, where R$^1$ and R$^2$ can optionally be taken together with intervening atoms to form a 3- to 10-membered, substituted or unsubstituted ring optionally containing one or more heteroatoms.

In some embodiments, R$^1$ is hydrogen. In some embodiments, R$^1$ is phenyl. In some embodiments, R$^1$ is optionally substituted C$_{1-6}$ aliphatic. In some embodiments, R$^1$ is n-butyl. In some embodiments, R$^1$ is n-propyl. In some embodiments, R$^1$ is ethyl. In some embodiments, R$^1$ is —CF$_3$. In some embodiments, R$^1$ is —CH$_2$Cl. In other embodiments, R$^1$ is methyl.

In some embodiments, R$^2$ is hydrogen. In some embodiments, R$^2$ is optionally substituted C$_{1-6}$ aliphatic. In some embodiments, R$^2$ is methyl.

In certain embodiments, R$^1$ and R$^2$ are taken together with intervening atoms to form a 3- to 10-membered, substituted or unsubstituted ring optionally containing one or more heteroatoms. In some embodiments, R$^1$ and R$^2$ are taken together with intervening atoms to form a cyclopentyl or cyclohexyl ring.

In certain embodiments, an epoxide is chosen from the group consisting of: ethylene oxide, propylene oxide, 1,2-butylene oxide, 2,3-butylene oxide, epichlorohydrin, cyclohexene oxide, cyclopentene oxide, 3,3,3-Trifluoro-1,2-epoxypropane, styrene oxide, a glycidyl ether, and a glycidyl ester.

In certain embodiments, the epoxide is ethylene oxide.

In certain embodiments, the epoxide is propylene oxide.

In certain embodiments, the carbonylation reaction occurring in the reactor in step (a) conforms to Scheme 2:

Scheme 2

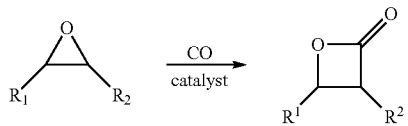

where, each of R$^1$ and R$^2$ is as defined above and described in classes and subclasses herein.

In certain embodiments, the carbonylation reaction conforms to Scheme 3:

Scheme 3

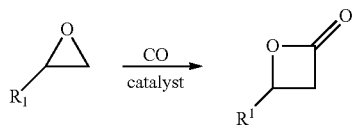

where, R$^1$ is selected from the group consisting of —H and C$_{1-6}$ aliphatic.

In certain embodiments, the carbonylation reaction conforms to Scheme 4 where the epoxide is propylene oxide and the carbonylation product is beta butyrolactone:

Scheme 4

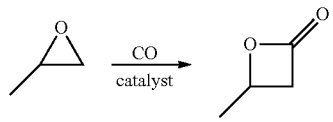

In certain embodiments, the carbonylation reaction comprises the reaction shown in Scheme 5 where the epoxide is ethylene oxide and the carbonylation product is betapropiolactone:

Scheme 5

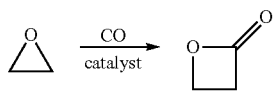

In certain embodiments, the carbonylation reaction occurring in the reactor in step (a) conforms to Scheme 6:

Scheme 6

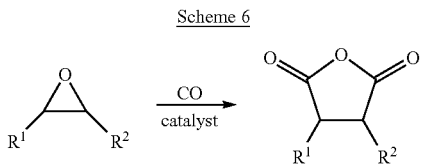

where, each of $R^1$ and $R^2$ is as defined above and described in classes and subclasses herein.

In certain embodiments, the carbonylation reaction conforms to Scheme 7:

Scheme 7

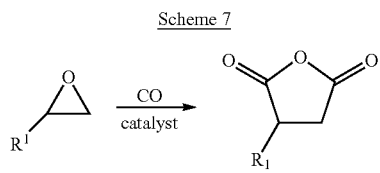

where, $R^1$ is selected from the group consisting of —H and $C_{1-6}$ aliphatic.

In certain embodiments, the carbonylation reaction conforms to Scheme 8 where the epoxide is propylene oxide and the carbonylation product is methylsuccinic anhydride:

Scheme 8

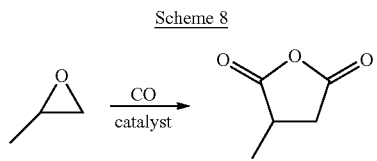

In certain embodiments, the carbonylation reaction comprises the reaction shown in Scheme 9 where the epoxide is ethylene oxide and the carbonylation product is succinic anhydride:

Scheme 9

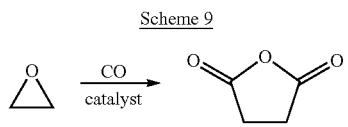

In certain embodiments, the carbonylation reaction conforms to Scheme 10 where the epoxide is propylene oxide and the carbonylation product is polyhydroxybutyrate:

Scheme 10

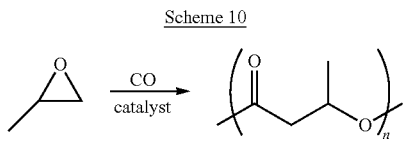

In certain embodiments, the carbonylation reaction comprises the reaction shown in Scheme 11 where the epoxide is ethylene oxide and the carbonylation product is polypropiolactone:

Scheme 11

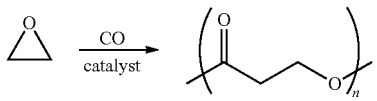

The carbon monoxide can be provide to the reactor in step (a) either as a pure stream or as a mixture of carbon monoxide and one or more additional gasses. In some embodiments, carbon monoxide is provided in a mixture with hydrogen (e.g., Syngas). The ratio of carbon monoxide and hydrogen can be any ratio, including by not limited to about 1:1, 1:2, 1:4, 1:10, 10:1, 4:1, 2:1 or a ratio between any two of these values. In some embodiments, the carbon monoxide is provided in mixture with gases as an industrial process gas.

Catalyst

Numerous carbonylation catalysts known in the art are suitable for (or can be adapted to) methods of the present invention. For example, in certain embodiments, the carbonylation methods utilize a metal carbonyl-Lewis acid catalyst such as those described in U.S. Pat. No. 6,852,865. In other embodiments, the carbonylation step is performed with one or more of the carbonylation catalysts disclosed in U.S. patent application Ser. No. 10/820,958; and Ser. No. 10/586,826. In other embodiments, the carbonylation step is performed with one or more of the catalysts disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In certain embodiments, the carbonylation catalyst includes a metal carbonyl compound. Typically, a single metal carbonyl compound is provided, but in certain embodiments, mixtures of two or more metal carbonyl compounds are provided. (Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more metal carbonyl compounds.) Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation.

In certain embodiments, a provided metal carbonyl compound comprises an anionic metal carbonyl moiety. In other embodiments, a provided metal carbonyl compound comprises a neutral metal carbonyl compound. In certain embodiments, a provided metal carbonyl compound comprises a metal carbonyl hydride or a hydrido metal carbonyl compound. In some embodiments, a provided metal carbonyl compound acts as a pre-catalyst which reacts in situ with one or more reaction components to provide an active species different from the compound initially provided. Such pre-catalysts are specifically encompassed by the present invention as it is recognized that the active species in a given reaction may not be known with certainty; thus the identification of such a reactive species in situ does not itself depart from the spirit or teachings of the present invention.

In certain embodiments, the metal carbonyl compound comprises an anionic metal carbonyl species. In certain embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In certain embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In certain embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$ $[V(CO)_6]^-$ $[Rh(CO)_4]^-$, $[Fe(CO)_4]^{2-}$ $[Ru(CO)_4]^{2-}$, $[Os(CO)_4]^{2-}$ $[Cr_2(CO)_{10}]^{2-}$ $[Fe_2(CO)_8]^{2-}$ $[Tc(CO)_5]^-$ $[Re(CO)_5]^-$ and $[Mn(CO)_5]^-$. In certain embodiments, the anionic metal carbonyl comprises $[Co(CO)_4]^-$. In some embodiments, a mixture of two or more anionic metal carbonyl complexes may be present in the carbonylation catalysts used in the methods.

The term "such as to provide a stable anionic metal carbonyl" for $[Q_dM'_e(CO)_w]^{y-}$" is used herein to mean that $[Q_dM'_e(CO)_w]^{y-}$ is a species characterizable by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the provided metal carbonyl compound is an anionic species, one or more cations must also necessarily be present. The present invention places no particular constraints on the identity of such cations. In certain embodiments, the cation associated with an anionic metal carbonyl compound comprises a reaction component of another category described hereinbelow. For example, in certain embodiments, the metal carbonyl anion is associated with a cationic Lewis acid. In other embodiments a cation associated with a provided anionic metal carbonyl compound is a simple metal cation such as those from Groups 1 or 2 of the periodic table (e.g. $Na^+$, $Li^+$, $K^+$, $Mg^{2+}$ and the like). In other embodiments a cation associated with a provided anionic metal carbonyl compound is a bulky non electrophilic cation such as an 'onium salt' (e.g. $Bu_4N^+$, $PPN^+$, $Ph_4P^+$ $Ph_4As^+$, and the like). In other embodiments, a metal carbonyl anion is associated with a protonated nitrogen compound (e.g. a cation may comprise a compound such as MeTBD-H$^+$, DMAP-H$^+$, DABCO-H$^+$, DBU-H$^+$ and the like). In certain embodiments, compounds comprising such protonated nitrogen compounds are provided as the reaction product between an acidic hydrido metal carbonyl compound and a basic nitrogen-containing compound (e.g. a mixture of DBU and $HCo(CO)_4$).

In certain embodiments, a catalyst utilized in the methods described above comprises a neutral metal carbonyl compound. In certain embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In certain embodiments, the neutral metal carbonyl has the general formula $QM'(CO)_{w'}$. In certain embodiments, the neutral metal carbonyl has the general formula $M'(CO)_{w'}$. In certain embodiments, the neutral metal carbonyl has the general formula $QM'_2(CO)_{w'}$. In certain embodiments, the neutral metal carbonyl has the general formula $M'_2(CO)_{w'}$. Suitable neutral metal carbonyl compounds include, but are not limited to: $Ti(CO)_7$; $V_2(CO)_{12}$; $Cr(CO)_6$; $Mo(CO)_6$; $W(CO)_6$ $Mn_2(CO)_{10}$, $Tc_2(CO)_{10}$, and $Re_2(CO)_{10}$ $Fe(CO)_5$, $Ru(CO)_5$ and $Os(CO)_5$ $Ru_3(CO)_{12}$, and $Os_3(CO)_{12}$ $Fe_3(CO)_{12}$ and $Fe_2(CO)_9$ $Co_4(CO)_{12}$, $Rh_4(CO)_{12}$, $Rh_6(CO)_{16}$, and $Ir_4(CO)_{12}$ $Co_2(CO)_8$ $Ni(CO)_4$.

The term "such as to provide a stable neutral metal carbonyl for $Q_dM'_e(CO)_{w'}$ is used herein to mean that $Q_dM'_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments, no ligands Q are present on the metal carbonyl compound. In other embodiments, one or more ligands Q are present on the metal carbonyl compound. In certain embodiments, where Q is present, each occurrence of Q is selected from the group consisting of phosphine ligands, amine ligands, cyclopentadienyl ligands, heterocyclic ligands, nitriles, phenols, and combinations of two or more of these. In certain embodiments, one or more of the CO ligands of any of the metal carbonyl compounds described above is replaced with a ligand Q. In certain embodiments, Q is a phosphine ligand. In certain embodiments, Q is a triaryl phosphine. In certain embodiments, Q is trialkyl phosphine. In certain embodiments, Q is a phosphite ligand. In certain embodiments, Q is an optionally substituted cyclopentadienyl ligand. In certain embodiments, Q is cp. In certain embodiments, Q is cp*. In certain embodiments, Q is an amine or a heterocycle.

In certain embodiments, the carbonylation catalyst utilized in the methods described above further includes a Lewis acidic component. In some embodiments, the carbonylation catalyst includes an anionic metal carbonyl complex and a cationic Lewis acidic component. In certain embodiments, the metal carbonyl complex includes a carbonyl cobaltate and the Lewis acidic co-catalyst includes a metal-centered cationic Lewis acid. In certain embodiments, an included Lewis acid comprises a boron compound.

In certain embodiments, where an included Lewis acid comprises a boron compound, the boron compound comprises a trialkyl boron compound or a triaryl boron compound. In certain embodiments, an included boron compound comprises one or more boron-halogen bonds. In certain embodiments, where an included boron compound comprises one or more boron-halogen bonds, the compound is a dialkyl halo boron compound (e.g. $R_2BX$), a dihalo monoalkly compound (e.g. $RBX_2$), an aryl halo boron compound (e.g. $Ar_2BX$ or $ArBX_2$), or a trihalo boron compound (e.g. $BCl_3$ or $BBr_3$).

In certain embodiments, where the included Lewis acid comprises a metal-centered cationic Lewis acid, the Lewis acid is a cationic metal complex. In certain embodiments, the cationic metal complex has its charge balanced either in part, or wholly by one or more anionic metal carbonyl moieties. Suitable anionic metal carbonyl compounds include those described above. In certain embodiments, there are 1 to 17 such anionic metal carbonyls balancing the charge of the metal complex. In certain embodiments, there are 1 to 9 such anionic metal carbonyls balancing the charge of the metal complex. In certain embodiments, there are 1 to 5 such anionic metal carbonyls balancing the charge of the metal complex. In certain embodiments, there are 1 to 3 such anionic metal carbonyls balancing the charge of the metal complex.

In certain embodiments, where carbonylation catalysts used in methods of the present invention include a cationic metal complex, the metal complex has the formula $[(L^c)_v M_b]^{z+}$, where:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In certain embodiments, provided Lewis acids conform to structure I:

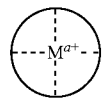

I wherein:

⊕ is a multidentate ligand;

M is a metal atom coordinated to the multidentate ligand;

a is the charge of the metal atom and ranges from 0 to 2; and

In certain embodiments, provided metal complexes conform to structure II:

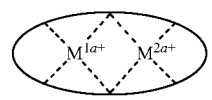

II

Where a is as defined above (each a may be the same or different), and $M^1$ is a first metal atom;

$M^2$ is a second metal atom;

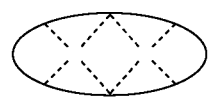

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net chage of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In certain embodiments, the multidentate ligand is a salen derivative. In other embodiments, the multidentate ligand is a porphyrin derivative. In other embodiments, the multidentate ligand is a tetraphenylporphyrin derivative. In other embodiments, the multidentate ligand is a corrole derivative.

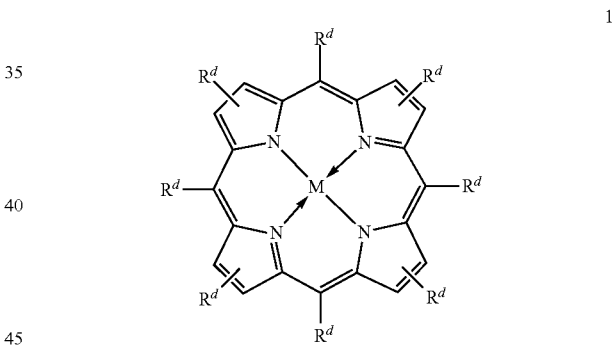

1

2

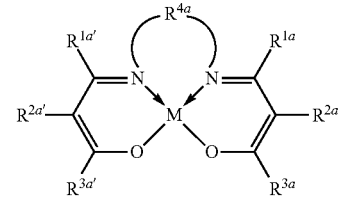

3

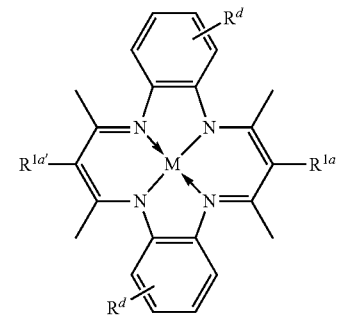

-continued

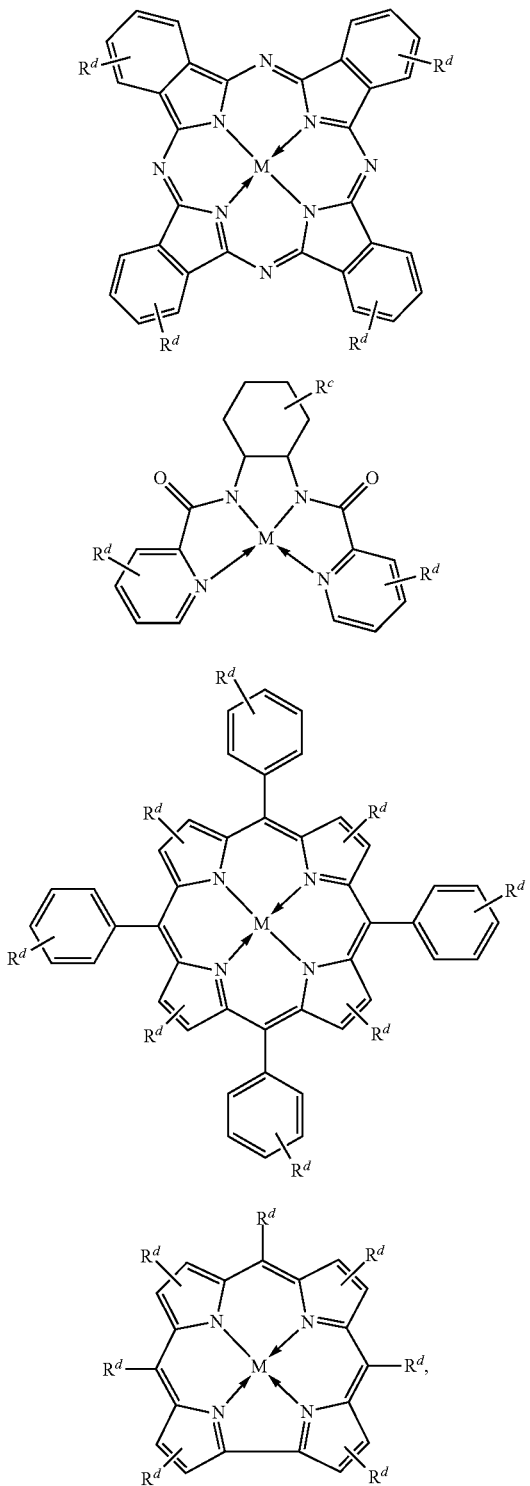

where each of $R^c$, $R^d$, $R^a$, $R^{1a}$, $R^{2a}$, $R^{3a}$, $R^{1a'}$, $R^{2a'}$, $R^{3a'}$, and M, is as defined and described in the classes and subclasses herein.

In certain embodiments, Lewis acids provided carbonylation catalysts used in methods of the present invention comprise metal-porphinato complexes. In certain embodiments, the moiety

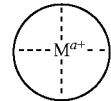

has the structure:

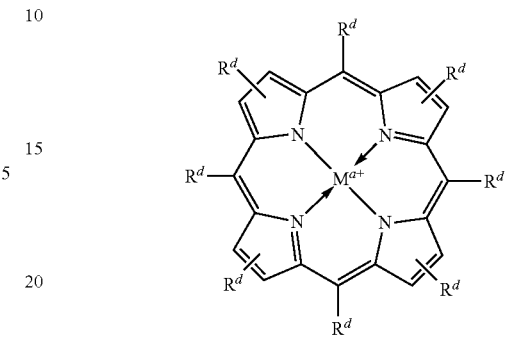

where each of M and a is as defined above and described in the classes and subclasses herein, and $R^d$ at each occurrence is independently hydrogen, halogen, —$OR^4$, —$NR^y{}_2$, —SR, —CN, —$NO_2$, —$SO_2R^y$, —$SOR^y$, —$SO_2NR^y{}_2$; —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, where each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ independently is a hydroxyl protecting group or $R^y$.

In certain embodiments, the moiety

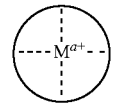

has the structure:

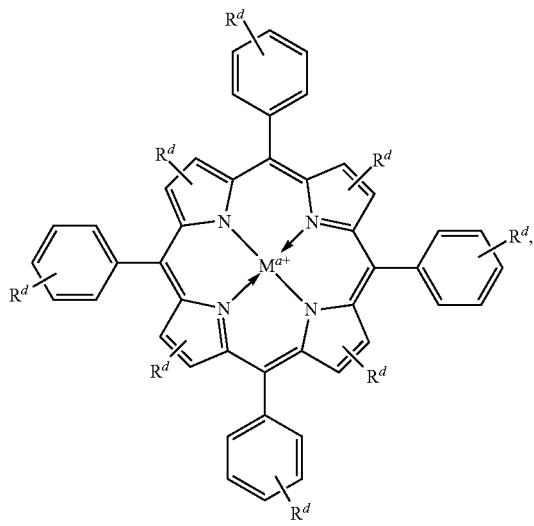

where M, a and $R^d$ are as defined above and in the classes and subclasses herein.

In certain embodiments, the moiety

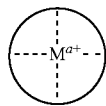

has the structure:

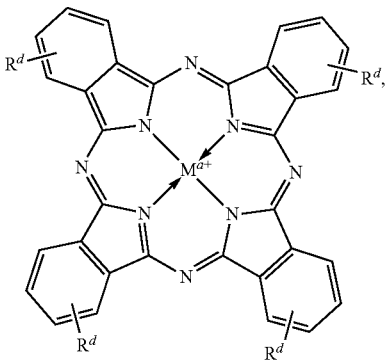

where M, a and $R^d$ are as defined above and in the classes and subclasses herein.

In certain embodiments, Lewis acids included in carbonylation catalysts used in methods of the present invention comprise metallo salenate complexes. In certain embodiments, the moiety

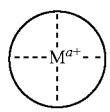

has the structure:

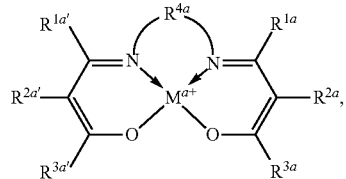

wherein:
M, and a are as defined above and in the classes and subclasses herein.
$R^{1a}$, $R^{1a'}$, $R^{2a}$, $R^{2a'}$, $R^{3a}$, and $R^{3a'}$ are independently hydrogen, halogen, —$OR^4$, —$NR^y_2$, —SR, —CN, —$NO_2$, —$SO_2R^y$, —SOR, —$SO_2NR^y_2$; —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each R, $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more R groups; and
$R^{4a}$ is selected from the group consisting of:

e)

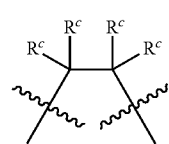

f)

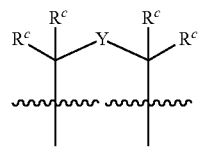

g)

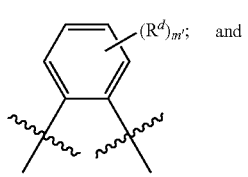

and h)

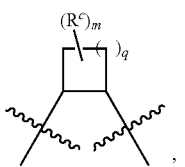

where
$R^c$ at each occurrence is independently hydrogen, halogen, —OR, —$NR^y_2$, —$SR^y$, —CN, —$NO_2$, —$SO_2R^y$, —$SOR^y$, —$SO_2NR^y_2$; —CNO, —$NRSO_2R^y$, —NCO, —N₃, —SiR₃; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:

two or more $R^c$ groups may be taken together with the carbon atoms to which they are attached and any intervening atoms to form one or more rings;

when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

Y is a divalent linker selected from the group consisting of: —NR$^y$—, —N(R)C(O)—, —C(O)NR$^y$—, —O—, —C(O)—, —OC(O)—, —C(O)O—, —S—, —SO—, —SO₂—, —C(=S)—, —C(=NR$^y$)—, —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive;

q is 0 or an integer from 1 to 4, inclusive; and x is 0, 1, or 2.

In certain embodiments, a provided Lewis acid comprises a metallo salen compound, as shown in formula Ia:

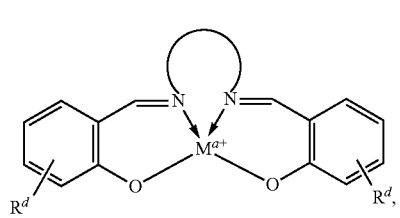

Ia wherein each of M, $R^d$, and a, is as defined above and in the classes and subclasses herein, ⌒ represents is an optionally substituted moiety linking the two nitrogen atoms of the diamine portion of the salen ligand, where ⌒ is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO₂—, —C(=S)—, —C(=NR$^y$)—, —C(=NOR$^y$)— or —N=N—.

In certain embodiments metal complexes having formula Ia above, at least one of the phenyl rings comprising the salicylaldehyde-derived portion of the metal complex is independently selected from the group consisting of:

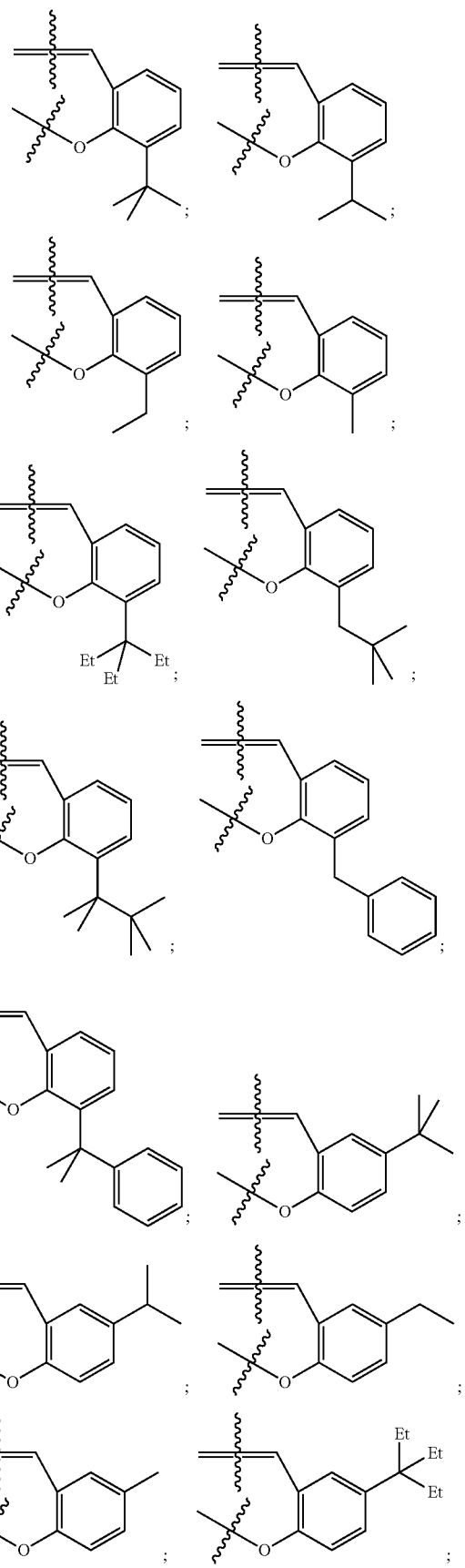

-continued
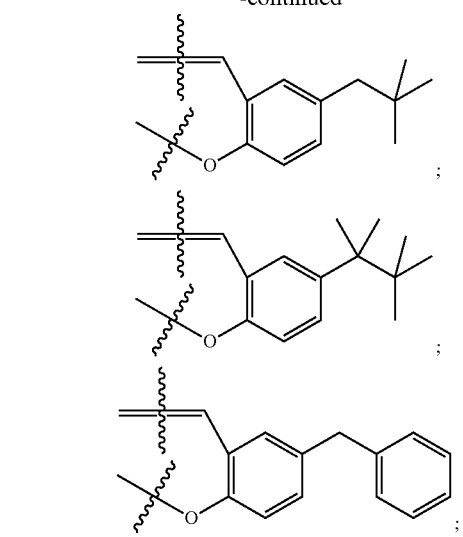
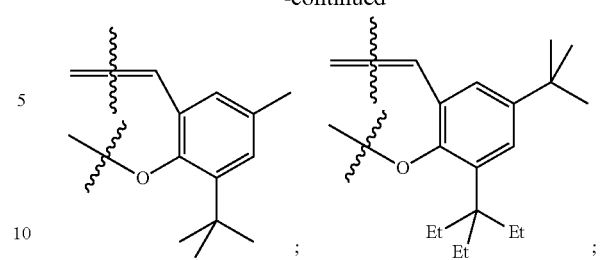
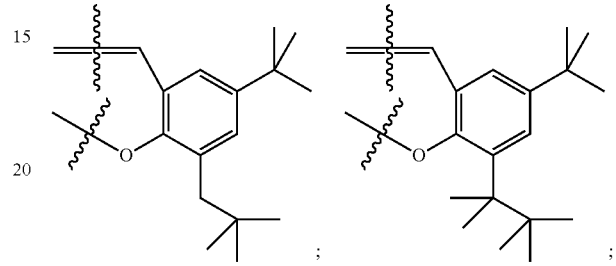
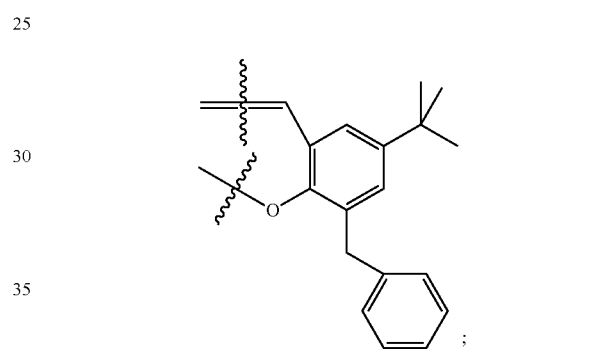
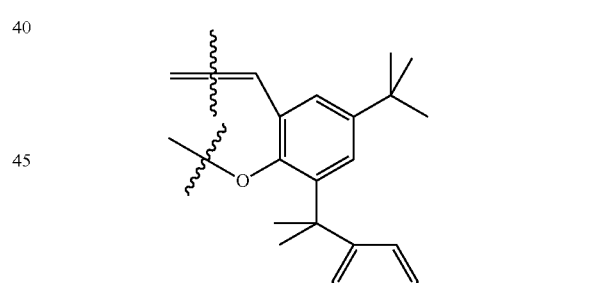
; and
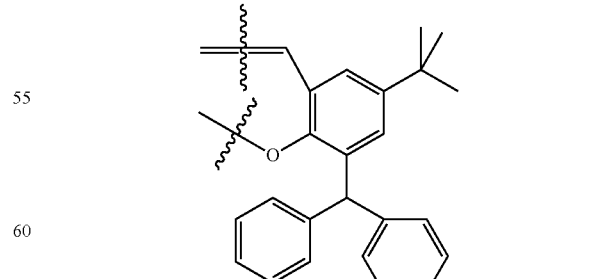
.
In certain embodiments, a provided Lewis acid comprises a metallo salen compound, conforming to one of formulae Va or Vb:

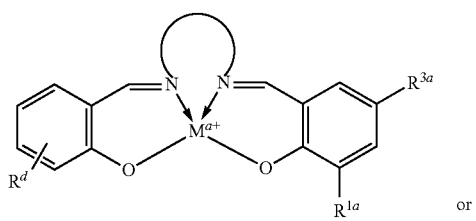

or

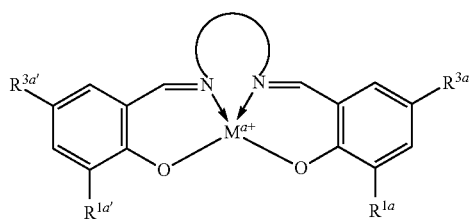

where M, a, $R^d$, $R^{1a}$, $R^{3a}$, $R^{1a'}$, $R^{3a'}$, and ⌒, are as defined above and in the classes and subclasses herein.

In certain embodiments of metal complexes having formulae Va or Vb, each $R^{1'}$ and $R^{3'}$ is, independently, optionally substituted $C_1$-$C_{20}$ aliphatic.

In certain embodiments, the moiety ⌒ comprises an optionally substituted 1,2-phenyl moiety.

In certain embodiments, Lewis acids included in carbonylation catalysts used in methods of the present invention comprise metal-tmtaa complexes. In certain embodiments, the moiety

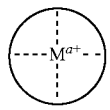

has the structure:

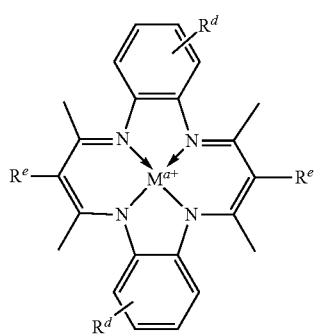

where M, a and $R^d$ are as defined above and in the classes and subclasses herein, and $R^e$ at each occurrence is independently hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In certain embodiments, the moiety

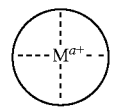

has the structure:

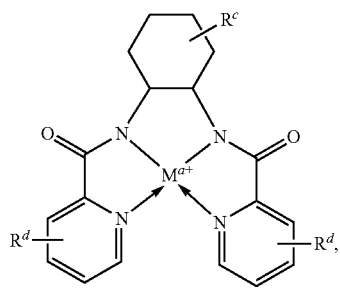

where each of M, a, $R^c$ and $R^d$ is as defined above and in the classes and subclasses herein.

In certain embodiments, where carbonylation catalysts used in methods of the present invention include a Lewis acidic metal complex, the metal atom is selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium.

In certain embodiments, M has an oxidation state of +2. In certain embodiments, M is Zn(II), Cu(II), Mn(II), Co(II), Ru(II), Fe(II), Co(II), Rh(II), Ni(II), Pd(II) or Mg(II). In certain embodiments M is Zn(II). In certain embodiments M is Cu(II).

In certain embodiments, M has an oxidation state of +3. In certain embodiments, M is Al(III), Cr(III), Fe(III), Co(III), Ti(III) In(III), Ga(III) or Mn(III). In certain embodiments M is Al(III). In certain embodiments M is Cr(III).

In certain embodiments, M has an oxidation state of +4. In certain embodiments, M is Ti(IV) or Cr(IV).

In certain embodiments, $M^1$ and $M^2$ are each independently a metal atom selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium. In certain embodiments, $M^1$ and $M^2$ are the same. In certain embodiments, $M^1$ and $M^2$ are the same metal, but have different oxidation states. In certain embodiments, $M^1$ and $M^2$ are different metals.

In certain embodiments, one or more of $M^1$ and $M^2$ has an oxidation state of +2. In certain embodiments, $M^1$ is Zn(II), Cu(II), Mn(II), Co(II), Ru(II), Fe(II), Co(II), Rh(II), Ni(II), Pd(II) or Mg(II). In certain embodiments $M^1$ is Zn(II). In certain embodiments $M^1$ is Cu(II). In certain embodiments, $M^2$ is Zn(II), Cu(II), Mn(II), Co(II), Ru(II), Fe(II), Co(II), Rh(II), Ni(II), Pd(II) or Mg(II). In certain embodiments $M^2$ is Zn(II). In certain embodiments $M^2$ is Cu(II).

In certain embodiments, one or more of $M^1$ and $M^2$ has an oxidation state of +3. In certain embodiments, $M^1$ is Al(III), Cr(III), Fe(III), Co(III), Ti(III) In(III), Ga(III) or Mn(III). In certain embodiments $M^1$ is Al(III). In certain embodiments $M^1$ is Cr(III). In certain embodiments, $M^2$ is Al(III), Cr(III), Fe(III), Co(III), Ti(III) In(III), Ga(III) or Mn(III). In certain embodiments $M^2$ is Al(III). In certain embodiments $M^2$ is Cr(III).

In certain embodiments, one or more of $M^1$ and $M^2$ has an oxidation state of +4. In certain embodiments, $M^1$ is Ti(IV) or Cr(IV). In certain embodiments, $M^2$ is Ti(IV) or Cr(IV).

In certain embodiments, the metal-centered Lewis-acidic component of the carbonylation catalyst includes a dianionic tetradentate ligand. In certain embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand.

In certain embodiments, the carbonylation catalyst includes a carbonyl cobaltate in combination with an aluminum porphyrin compound.

In certain embodiments, the carbonylation catalyst includes a carbonyl cobaltate in combination with a chromium porphyrin compound.

In certain embodiments, the carbonylation catalyst includes a carbonyl cobaltate in combination with a chromium salen compound. In certain embodiments, the carbonylation catalyst includes a carbonyl cobaltate in combination with a chromium salophen compound.

In certain embodiments, the carbonylation catalyst includes a carbonyl cobaltate in combination with an aluminum salen compound. In certain embodiments, the carbonylation catalyst includes a carbonyl cobaltate in combination with an aluminum salophen compound.

In certain embodiments, one or more neutral two electron donors coordinate to M $M^1$ or $M^2$ and fill the coordination valence of the metal atom. In certain embodiments, the neutral two electron donor is a solvent molecule. In certain embodiments, the neutral two electron donor is an ether. In certain embodiments, the neutral two electron donor is tetrahydrofuran, diethyl ether, acetonitrile, carbon disulfide, or pyridine. In certain embodiments, the neutral two electron donor is tetrahydrofuran. In certain embodiments, the neutral two electron donor is an epoxide. In certain embodiments, the neutral two electron donor is an ester or a lactone.

Solvents

In some embodiments, the carbonylation methods herein are performed in a solvent. In certain embodiments, the solvent is fed to the continuous carbonylation reactor in step (a) as a separate stream. In other embodiments, the solvent may be fed to the ractor along with the catalyst the epoxide or another feedstream entering the carbonylation reactor. In certain embodiments, the solvent enters the carbonylation reactor along with the carbonylation catalyst which is provided as a catalyst solution in the solvent. In certain embodiments, the solvent enters the carbonylation reactor in two or more separate feedstreams. In embodiments where solvent is present in the carbonylation reactor, it is also present in the carbonylation product stream.

The solvent may be selected from any solvent, and mixtures of solvents. Additionally, beta-lactone may be utilized as a co-solvent. Solvents most suitable for the methods include ethers, hydrocarbons and non protic polar solvents. Examples of suitable solvents include, but are not limited to: tetrahydrofuran ("THF"), sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, dimethoxy ethane, acetone, and methylethyl ketone.

In some embodiments, the carbonylation methods further include a Lewis base additive in the carbonylation reactor. In certain embodiments such Lewis base additives can stabilize or reduce deactivation of the catalysts. In some embodiments, the Lewis base additive is selected from the group consisting of phosphines, amines, guanidines, amidines, and nitrogen-containing heterocycles. In some embodiments, the Lewis base additive is a hindered amine base. In some embodiments, the Lewis base additive is a 2,6-lutidine; imidazole, 1-methylimidazole, 4-dimethylaminopyridine, trihexylamine and triphenylphosphine.

Carbonylation Reaction Conditions

The carbonylation reaction conditions in step (a) of the methods above are preferably selected to effect efficient conversion of the epoxide to the desired product(s). Temperature, pressure, mixing, and reaction time influence reaction speed and efficiency. Additionally the ratio of reactants to each other and to the catalyst effect reaction speed and efficiency. The control and optimization of these parameters is a routine matter in the field of chemical engineering and the present invention places no particular constraints or limitations on the carbonylation reaction conditions.

In some embodiments, the reaction temperature can range from between about −20° C., to about 600° C. In some embodiments, the reaction temperature is about −20° C., about 0° C., about 20° C., about 40° C., about 60° C., about 80° C., about 100° C., about 200° C., about 300° C., about 400° C., about 500° C. or about, about 600° C. In some embodiments, the temperature is in a range between about 40° C. and about 120° C. In some embodiments, the temperature is in a range between about 60° C. and about 140° C. In some embodiments, the temperature is in a range between about 40° C. and about 80° C. In some embodiments, the temperature is in a range between about 50° C. and about 70° C. In some embodiments, the reactants, catalyst and solvent are supplied to the reactor at standard temperature, and then heated in the reactor. In some embodiments, the reactants are pre-heated before entering the reactor.

In some embodiments, the reaction pressure can range from between about 50 psig to about 5000 psig. In some embodiments, the reaction pressure is about 100 psig, about 200 psig, about 300 psig, about 400 psig, about 500 psig, about 600 psig, about 700 psig, about 800 psig, about 900 psig, or about 1000 psig. In some embodiments, the pressure ranges from about 50 psig to about 2000 psig. In some embodiments, the pressure ranges from about 100 psig to 1000 psig. In some embodiments, the pressure ranges from about 200 psig to about 800 psig. In some embodiments, the pressure ranges from about 800 psig to about 1600 psig. In some embodiments, the pressure ranges from about 1500 psig to about 3500 psig. In some embodiments, the pressure ranges from about 3000 psig to about 5500 psig. In some embodiments, the reaction pressure is supplied entirely by the carbon monoxide. For example, carbon monoxide is added to the at reactor at high pressure to increase pressure to the reaction pressure. In some embodiments, all reactants, solvent and catalyst are supplied to the reactor at reaction pressure.

In some embodiments, the ratio of catalyst to epoxide is selected, based on other reaction conditions, so that the reaction proceeds in an economical and time-feasible manner. In some embodiments, the ratio of catalyst to epoxide is about 1:10000 on a molar basis. In some embodiments, the molar ratio of catalyst to epoxide is about 1:5000, is about 1:2500, is about 1:2000, is about 1:1500, is about 1:1000, is about 1:750, is about 1:500, is about 1:250, is about 1:200, is about 1:150, or is about 1:100. In some embodiments, the concentration of the epoxide is in the range between about 0.1 M and about 5.0 M. In some embodiments, the concentration of the epoxide is in the range between about 0.5 M and about 3.0 M.

In some embodiments, the reaction is maintained for a period of time sufficient to allow complete, near complete reaction of the epoxide to carbonylation products or as complete as possible based on the reaction kinetics and or reaction conditions. In some embodiments, the reaction time is a residence time in the carbonylation reactor in step (a). In certain embodiments, the residence time is about 12 hours, about 8 hours, about 6 hours, about 3 hours, about 2 hours or about 1 hour. In certain embodiments, the residence time is about 30 minutes, about 20 minutes, about 15 minutes, about 10 minutes, about 5 minutes, about 3 minutes, about 2 minutes, or about 1 minute. In certain embodiments, the residence time is less than 1 minute.

Carbonylation Reaction Products

The reaction product stream formed in step (a) of the methods herein may contain reaction by-products, un-reacted reactants, as well as catalyst and the desired carbonylation product. In some embodiments, the un-reacted reactants include epoxide or carbon monoxide. As such, the reaction may not proceed to completion and may be considered a partial reaction.

In some embodiments, where the product of the carbonylation is a beta lactone, an amount of un-reacted epoxide is maintained sufficient to prevent the formation of a succinic anhydride by further carbonylation of the beta lactone. Without being bound by a particular theory, it is speculated that the second reaction converting the beta-lactone to succinic anhydride does not proceed unless substantially all of the epoxide is consumed. Thus a remaining portion of the epoxide feed to the reactor that exits un-reacted appears to prevent the formation of succinic anhydride. Therefore, in some embodiments, the reaction product stream contains unconverted epoxide in an amount of at least about 5% epoxide, at least 3% epoxide, at least about 1% epoxide or at least about 0.1%, by weight.

Reaction Mode

The methods herein place no particular limits on the type, size or geometry of the reactor employed and indeed, in some cases, more than one reactor may be employed. It is to be understood that the term "reactor" as recited in the methods herein may actually represent more than one physical reactor (for example the reactor could be a train of continuous stirred tank reactors (CSTRs) connected in parallel or in series, or a plurality of plug flow reactors). In certain embodiments, the "reactor" referred to in the methods herein may also comprise more than one type of reactor (for example the reactor could comprise a CSTR in series with a plug flow reactor). Many such combinations are known in the art and could be employed by the skilled artisan to achieve an efficient reaction in step (a) of the methods described herein.

EXAMPLES

In a first example of a process according to the present invention, a continuous stirred tank reactor is fed with an ethylene oxide stream, a catalyst stream comprising a THF solution of a carbonylation catalyst where the catalyst consists of the combination of chromium (III) salph complex and carbonyl cobaltate, and a carbon monoxide stream. The reactor is maintained at a temperature of 60° C. by heating, and maintained at 600 psig by feeding carbon monoxide on demand to a headspace within the reactor at that pressure. The reaction volume in the reactor is maintained at a constant level by withdrawing a reaction product stream from the reactor at a mass flow rate corresponding to the sum of the mass flows entering the reactor. The catalyst and EO feeds are maintained at a rate such that the chemical composition of the reactor contents are maintained at a steady state wherein the reaction mixture contains between 0.2 and 2 weight percent ethylene oxide, and between 20 and 60 weight percent beta propiolactone. The reaction product stream is directed first to a flash chamber maintained at a reduced pressure (e.g. between about 0.1 and 0.8 bar). Volatiles released from the reaction product stream in the flash chamber are recompressed and recycled. The reaction product stream is pumped from the flash chamber and flowed through a packed column containing beads of a sodium-form cation exchange resin. The resin exchanges sodium atoms for the cationic Lewis acid in the product stream to provide a first intermediate product stream substantially free of the cationic Lewis acid and containing sodium carbonyl cobaltate. The first intermediate product stream is fed to a second column containing the chloride form of an anion exchange resin to provide a second intermediate product stream containing THF, beta propiolactone and suspended sodium chloride. The second intermediate product stream is fed to a distillation unit where the THF and beta propiolactone are fractionated. The beta propiolactone is carried forward to another process while the THF is recycled. Solids primarily consisting of sodium chloride along with small amounts of polymerized products and catalyst residues are disposed of as waste.

The reactor is operated in this way for a first interval of 12 hours during which time the two ion exchange columns have accumulated catalyst residues and become substantially saturated with cationic Lewis acid and carbonyl cobaltate. At this time the saturated columns are removed from the reaction product pathway and replaced with fresh columns. The saturated exchange columns are treated with brine to elute the catalyst components which are extracted into a suitable organic solvent, recombined and purified to provide a new batch of carbonylation catalyst which is stored and fed to the reactor in a future time interval. Meanwhile, the eluted columns are processed to ready them for return to service in the process.

In a second example of a process according to the present invention, a continuous stirred tank reactor is fed with an ethylene oxide stream, a catalyst stream comprising a dioxane solution of tetraphenylporphyrinato aluminum carbonyl cobaltate, and a carbon monoxide stream. The reactor is maintained at a temperature of 60° C. by heating, and maintained at 600 psig by feeding carbon monoxide on demand to a headspace within the reactor at that pressure. The reaction volume in the reactor is maintained at a constant level by withdrawing a reaction product stream from the reactor at a flow rate corresponding to the sum of the flows entering the reactor. The catalyst and EO feeds are maintained at rates such that the chemical composition of the reactor contents are maintained at a steady state wherein the reaction mixture contains between 0.2 and 2 weight percent ethylene oxide, and between 20 and 60 weight percent beta propiolactone. The reaction product stream is maintained under 600 psig of CO pressure and directed through a resin column containing the chloride form of an anion exchange resin. The resin exchanges chloride atoms for the carbonyl cobaltate in the product stream to provide a first intermediate product stream substantially free of the cobalt carbonyl and containing tetraphenylporphyrinato aluminum chloride. A non-polar high boiling hydrocarbon is injected into the first intermediate product stream and the stream is pumped through a combined static mixer and heat exchanger such that it is cooled to a sub-ambient temperature and the tetraphenylporphyrinato aluminum chloride precipitates. This stream is fed through a filter unit to accumulate the solids while the filtrate from this unit is directed to a distillation unit where the dioxane and beta-propiolactone are separated. The isolated beta propiolactone is carried forward to another process while the dioxane is recycled. The heavies from the distillation unit consisting primarily of the high boiling hydrocarbon are cooled and recycled.

The reactor is operated in this way for a first interval of 12 hours during which time the anion exchange column accumulates carbonyl cobaltate until it is substantially saturated. At this time the saturated column is removed from the reaction product pathway and replaced with a fresh anion exchange column. The saturated exchange column is treated with brine to elute sodium carbonyl cobaltate which is purified and used to generate new carbonylation catalyst by combining it with chloride salt of the Lewis acid recovered from the filtration unit. The resulting batch of carbonylation catalyst is stored and fed to the reactor during a future time interval. Meanwhile, the eluted anion exchange column is processed to ready it for return to service in the process during a future interval.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for the continuous reaction of an epoxide and carbon monoxide comprising:
    a) feeding a continuous carbonylation reactor during a first interval of time with a catalyst feed stream comprising a carbonylation catalyst, where within the reactor, an epoxide and carbon monoxide react in the presence of the carbonylation catalyst to provide a reaction product stream comprising an epoxide carbonylation product and carbonylation catalyst,
    wherein the carbonylation catalyst comprises a metal carbonyl compound in combination with one or more other catalyst components,
        wherein the metal carbonyl compound comprises an anionic metal carbonyl in combination with a cationic Lewis acid,
            wherein the anionic metal carbonyl is selected from the group consisting of: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$ and $[Mn(CO)_5]^-$ or a mixture of two or more thereof;
    b) treating the reaction product stream to separate at least a portion of the carbonylation catalyst from the reaction product stream,
    c) accumulating the metal carbonyl compound of the carbonylation catalyst removed in step (b) throughout the first interval of time, and
    d) feeding a continuous carbonylation reactor during a second interval of time with a catalyst feed stream wherein at least a portion of the carbonylation catalyst in the catalyst feed stream contains the metal carbonyl compound accumulated in step (c),
    wherein the epoxide is selected from the group consisting of: ethylene oxide, propylene oxide, 1,2-butylene oxide, 2,3-butylene oxide, epichlorohydrin, cyclohexene oxide, cyclopentene oxide, 3,3,3-trifluoro-1,2-epoxypropane, styrene oxide, a glycidyl ether, and a glycidyl ester.

2. The method of claim 1, wherein the epoxide is ethylene oxide.

3. The method of claim 2, wherein the epoxide carbonylation product comprises beta propiolactone, succinic anhydride, polypropiolactone, 3-hydroxypropionic acid, or a 3-hydroxypropionate ester, or any combination thereof.

4. The method of claim 2, wherein the epoxide carbonylation product comprises beta propiolactone.

5. A method for the continuous reaction of an epoxide and carbon monoxide comprising:
    a) feeding a continuous carbonylation reactor during a first interval of time with a catalyst feed stream comprising a carbonylation catalyst, where within the reactor, an epoxide and carbon monoxide react in the presence of the carbonylation catalyst to provide a reaction product stream comprising an epoxide carbonylation product and carbonylation catalyst,
    wherein the carbonylation catalyst comprises a metal carbonyl compound comprising a metal carbonyl,
        wherein the metal carbonyl is selected from the group consisting of: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$, or a mixture of two or more thereof;
    b) treating the reaction product stream with a solvent selected from the group consisting of: condensed phase $CO_2$, an alkane, an aliphatic hydrocarbon, and an aromatic hydrocarbon thereby causing at least a portion of the carbonylation catalyst to precipitate from the reaction product stream,
    c) separating the carbonylation catalyst that precipitated from the reaction product stream,
    d) accumulating the metal carbonyl compound of the carbonylation catalyst removed throughout the first interval of time, and
    e) feeding a continuous carbonylation reactor during a second interval of time with a catalyst feed stream wherein at least a portion of the carbonylation catalyst in the catalyst feed stream contains the metal carbonyl compound accumulated in step (d),
    wherein the epoxide is selected from the group consisting of: ethylene oxide, propylene oxide, 1,2-butylene oxide, 2,3-butylene oxide, epichlorohydrin, cyclohexene oxide, cyclopentene oxide, 3,3,3-trifluoro-1,2-epoxypropane, styrene oxide, a glycidyl ether, and a glycidyl ester.

6. The method of claim 5, wherein the epoxide is ethylene oxide.

7. The method of claim 6, wherein the epoxide carbonylation product comprises beta propiolactone, succinic anhydride, polypropiolactone, 3-hydroxypropionic acid, or a 3-hydroxypropionate ester, or any combination thereof.

8. The method of claim 6, wherein the epoxide carbonylation product comprises beta propiolactone.

9. A method for the continuous reaction of an epoxide and carbon monoxide comprising:
  a) feeding a continuous carbonylation reactor during a first interval of time with a catalyst feed stream comprising a carbonylation catalyst, where within the reactor, an epoxide and carbon monoxide react in the presence of the carbonylation catalyst to provide a reaction product stream comprising an epoxide carbonylation product and carbonylation catalyst,
  wherein the carbonylation catalyst comprises a metal carbonyl compound comprising a metal carbonyl,
    wherein the metal carbonyl is selected from the group consisting of: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]-$, or a mixture of two or more thereof;
  b) adding to the reaction product stream an extraction solvent selected from the group consisting of: water, condensed phase $CO_2$, and an ionic liquid, causing formation of two phases, wherein the carbonylation catalyst is at least partially partitioned from the reaction product stream across two phases,
  c) accumulating the metal carbonyl compound of the carbonylation catalyst removed in step (b) throughout the first interval of time, and
  d) feeding a continuous carbonylation reactor during a second interval of time with a catalyst feed stream wherein at least a portion of the carbonylation catalyst in the catalyst feed stream contains the metal carbonyl compound accumulated in step (c),
  wherein the epoxide is selected from the group consisting of: ethylene oxide, propylene oxide, 1,2-butylene oxide, 2,3-butylene oxide, epichlorohydrin, cyclohexene oxide, cyclopentene oxide, 3,3,3-trifluoro-1,2-epoxypropane, styrene oxide, a glycidyl ether, and a glycidyl ester.

10. The method of claim 9, wherein the epoxide is ethylene oxide.

11. The method of claim 10, wherein the epoxide carbonylation product comprises beta propiolactone, succinic anhydride, polypropiolactone, 3-hydroxypropionic acid, or a 3-hydroxypropionate ester, or any combination thereof.

12. The method of claim 10, wherein the epoxide carbonylation product comprises beta propiolactone.

13. The method of claim 1, wherein step (b) further comprises removing the metal carbonyl compound of the carbonylation catalyst from the reaction product stream by an anionic exchange material.

14. The method of claim 1, wherein step (b) further comprises a step of adding a solvent selected from a group consisting of: condensed phase $CO_2$, an alkane, an aliphatic hydrocarbon, and an aromatic hydrocarbon to cause the carbonylation catalyst to precipitate from the reaction product stream and a step of separating the precipitated carbonylation catalyst from the reaction product stream.

15. The method of claim 1, wherein step (b) further comprises a step of treating the carbonylation catalyst of the reaction product stream with a solid material, wherein the solid material adsorbs at least a portion of the carbonylation catalyst from the reaction product stream.

16. The method of claim 15, wherein the solid material is a organic substance or an inorganic adsorbing material that have undergone chemical treatments to enhance affinity of the catalyst.

17. The method of claim 1, wherein step (b) further comprises a step of adding an extraction solvent, wherein the extraction solvent is selected from the group consisting of: water, condensed phase $CO_2$, and an ionic liquid, and wherein the carbonylation catalyst is at least partially partitioned from the reaction product stream.

18. The method of claim 5, wherein the step (c) of separating the carbonylation catalyst from the reaction product stream is performed using filtration, sedimentation, centrifugation, coagulation, or a combination thereof.

19. The method of claim 9, wherein the extraction solvent is an ionic liquid and the ionic liquid is selected from the group consisting of: ammonium, tetralkylammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium, uronium, and any combination of two or more of these.

* * * * *